United States Patent
Sandberg

(10) Patent No.: US 7,774,210 B1
(45) Date of Patent: Aug. 10, 2010

(54) METHOD AND SYSTEM FOR RECORDING AND MAINTAINING PATIENT HISTORY DATA AS WELL AS GENERATING CONCURRENT BILLING RECORDS

(75) Inventor: Dale Sandberg, Pleasant Grove, UT (US)

(73) Assignee: DHI Computing Service, Inc., Provo, UT (US)

( * ) Notice: Subject to any disclaimer, the term of this patent is extended or adjusted under 35 U.S.C. 154(b) by 0 days.

(21) Appl. No.: 09/476,415

(22) Filed: Dec. 30, 1999

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. .................. 705/2; 705/3; 705/4
(58) Field of Classification Search ............. 705/2–3, 705/4
See application file for complete search history.

(56) References Cited

U.S. PATENT DOCUMENTS

| | | | | |
|---|---|---|---|---|
| 4,549,264 A | | 10/1985 | Carroll et al. ............. 705/32 |
| 4,553,206 A | * | 11/1985 | Smutek et al. ............. 1/1 |
| 4,831,526 A | * | 5/1989 | Luchs et al. ............. 705/4 |
| 4,893,270 A | | 1/1990 | Beck et al. ............. 700/90 |
| 5,072,383 A | * | 12/1991 | Brimm et al. ............. 705/2 |
| 5,247,611 A | * | 9/1993 | Norden-Paul et al. ....... 707/504 |
| 5,325,293 A | | 6/1994 | Dorne ............. 705/2 |
| 5,619,708 A | * | 4/1997 | Ho ............. 715/506 |
| 5,664,207 A | * | 9/1997 | Crumpler et al. ............. 707/505 |
| 5,682,526 A | | 10/1997 | Smokoff et al. ............. 707/104.1 |
| 5,704,371 A | | 1/1998 | Shepard ............. 128/897 |
| 5,732,221 A | * | 3/1998 | Feldon et al. ............. 705/3 |
| 5,737,539 A | * | 4/1998 | Edelson et al. ............. 705/3 |
| 5,745,712 A | * | 4/1998 | Turpin et al. ............. 345/763 |
| 5,772,585 A | * | 6/1998 | Lavin et al. ............. 600/300 |
| 5,781,442 A | | 7/1998 | Engleson et al. ............. 700/214 |
| 5,794,208 A | * | 8/1998 | Goltra ............. 705/3 |
| 5,812,984 A | * | 9/1998 | Goltra ............. 705/3 |
| 5,823,948 A | | 10/1998 | Ross, Jr. et al. ............. 600/300 |
| 5,823,949 A | * | 10/1998 | Goltra ............. 600/300 |

(Continued)

OTHER PUBLICATIONS

Kenneth KW Ong, Peter LB Chia, Expert Clinical Interface, IEEE, Computers in Cardiology, 1995, pp. 765-768.*

(Continued)

*Primary Examiner*—Gerald J. O'Connor
*Assistant Examiner*—Amber Altschul
(74) *Attorney, Agent, or Firm*—David B. Tingey; Kirton & McConkie

(57) ABSTRACT

A record and billing service system and method for use in health care offices. The system allows a health care agent to generate a visit form for a patient that keeps a record of the patient's health history and treatment records received at a healthcare facility. The visit form includes procedure and/or diagnoses information that is particular to a given health care provider or facility. Thus, the system generates the visit form, which shows the types of procedures, diagnosis, inventory, and the like normally provided in the health care office by the health care provider. The application can be customized to reflect specialties provided in that office or by that provider. The system also converts the types of procedures, diagnosis and inventory matters listed in the application into accurate billing records.

11 Claims, 14 Drawing Sheets

U.S. PATENT DOCUMENTS

| | | | |
|---|---|---|---|
| 5,832,450 A | 11/1998 | Myers et al. | 705/3 |
| 5,835,897 A | 11/1998 | Dang | 705/2 |
| 5,839,112 A * | 11/1998 | Schreitmueller et al. | 705/4 |
| 5,842,175 A * | 11/1998 | Andros et al. | 705/3 |
| 5,845,253 A | 12/1998 | Rensimer et al. | 705/2 |
| 5,845,255 A * | 12/1998 | Mayaud | 705/3 |
| 5,899,998 A | 5/1999 | McGauley et al. | 707/104.1 |
| 5,908,383 A * | 6/1999 | Brynjestad | 600/300 |
| 5,912,818 A | 6/1999 | McGrady et al. | 700/232 |
| 5,924,074 A * | 7/1999 | Evans | 705/3 |
| 5,930,799 A * | 7/1999 | Tamano et al. | 707/102 |
| 5,946,659 A * | 8/1999 | Lancelot et al. | 705/3 |
| 5,950,168 A * | 9/1999 | Simborg et al. | 705/3 |
| 5,991,728 A * | 11/1999 | DeBusk et al. | 705/2 |
| 6,014,630 A * | 1/2000 | Jeacock et al. | 705/3 |
| 6,047,259 A * | 4/2000 | Campbell et al. | 705/3 |
| 6,055,541 A * | 4/2000 | Solecki et al. | 707/103 R |
| 6,073,106 A * | 6/2000 | Rozen et al. | 705/3 |
| 6,081,786 A * | 6/2000 | Barry et al. | 705/3 |
| 6,151,581 A * | 11/2000 | Kraftson et al. | 705/3 |
| 6,283,761 B1 * | 9/2001 | Joao | 434/236 |
| 6,338,039 B1 * | 1/2002 | Lonski et al. | 705/3 |
| 6,341,265 B1 * | 1/2002 | Provost et al. | 705/4 |
| 6,393,404 B2 * | 5/2002 | Waters et al. | 705/2 |
| 6,401,072 B1 * | 6/2002 | Haudenschild et al. | 705/3 |
| 6,434,531 B1 * | 8/2002 | Lancelot et al. | 705/3 |
| 6,594,634 B1 * | 7/2003 | Hampton et al. | 705/3 |

OTHER PUBLICATIONS

Jorg Hohnloser & Florian Purner, PADS (Patient Archiving and Documentation System): A computerized patient record with educational aspects, International Journal of Clinical Monitoring and Computing 9: pp. 71-84, 1992.*

Ronald B. Melles, MD, Talmadge Cooper III, MD, George Peredy, MD, User Interface Preferences in a Point-of-care Data System, Permanente Clinical Information Systems, Kaiser Permanente Northern California Region, 1998.*

M. Dugas, MD, M.Sc., K. Uberla, M.D., M.Sc., Intranet-based clinical data entry, Institute for Medical Informatics, University of Munich, D-81377 Munich Germany, 1999.*

John A. Blackman, MD, The Usefulness of Handheld Computers in a Surgical Group Practice, Masters Thesis, Oregon Health Sciences University School of Medicine, May 1999.*

* cited by examiner

| 06/17/1999 | | Eye Care Clinic | | | | Page 1 | |
|---|---|---|---|---|---|---|---|
| | | Transaction History For Account 1000 (Anderson, Jeremy) from 7-1999 | | | | | |
| Period TranDate | Patient Name | Type | Code Description | Amount | Qty | Visit | Batch |
| 8-1999 06/17/1999 | Anderson, Susan | C | 99214 Office Visit Level 4-Est Patient | 80.00 | 0 | 167 | VT |
| 8-1999 06/17/1999 | Anderson, Susan | A | BCWO BlueCross/Blue Shield Write-off | -19.00 | 0 | 167 | VT ADJ |
| 8-1999 06/17/1999 | Anderson, Susan | C | 65205 Foreign Body Removal | 60.00 | 0 | 167 | VT |
| 8-1999 06/17/1999 | Anderson, Susan | A | BCWO BlueCross/Blue Shield Write-off | -10.00 | 0 | 167 | VT ADJ |
| 8-1999 06/17/1999 | Anderson, Susan | C | 68899 Unlisted Procedure, lacrimal sys | 22.00 | 0 | 167 | VT |
| 8-1999 06/17/1999 | Anderson, Susan | C | V2020 COntact Lens Materials | 20.00 | 0 | 167 | VT |
| 8-1999 06/17/1999 | Anderson, Susan | P | PPCK Personal Payment-Check | -60.00 | 0 | 167 | VT |
| 8-1999 06/17/1999 | Anderson, Susan | C | TAX Sales Tax | 1.25 | 0 | 167 | VT ADJ |
| 8-1999 06/17/1999 | Anderson, Susan | A | DISC Discount | -3.00 | 0 | 167 | VT |
| 8-1999 | | | Subtotal for this Period | 91.25 ** | | | |
| | | | Current Account Total Due | 3,751.75 *** | | | |

Fig. 16

METHOD AND SYSTEM FOR RECORDING AND MAINTAINING PATIENT HISTORY DATA AS WELL AS GENERATING CONCURRENT BILLING RECORDS

BACKGROUND OF THE INVENTION

The present invention relates generally to maintaining medical records of patients within a health care organization and, more specifically, to maintaining and updating medical records in a computer network system that also provides concurrent billing records reflective of the value of the services rendered.

Record keeping is critically important in the health care industry. Computerized health record data bases have been provided in the health care industry in recent years. The use of these data bases allows for a record of the patient to be maintained, which aids the health care provider in evaluating the patient's health and treatment history with that particular health care organization. Further, the recording of health care history for a group of patients is useful in conducting medical research for individuals having like symptoms and like treatments. Further still, the advantage of having computerized data bases aids in managing costs and providing billing records for the health care provider, the patient, the insurance providers, as well as any governmental health care program such as for example, Medicare.

In the past, the input of medical history information for a given patient was provided either by the health care provider directly via a recording system or was transcribed by a staff member from a physician's notes of a visit with a particular patient. These records would then be placed within a computerized data base for later recall. However, it was not easy to discern what were the costs to the patient for the treatment provided by the physician or for the services rendered by the health care organization in such a transcription. Even with this method and system for recording patient histories within a common data base, there is still a need to provide accurate billing information to the patient and to the doctor at any given time. The system provided for a billing invoice to be provided, but only after the doctor's notes had been sent to the accounting department and billing records personnel, which would either be discussed with the patient prior to leaving or sent to the patient at a later date following the actual visit. Neither the doctor nor the patient knew what the costs of the services would be until after the visit had been concluded and the patient had visited with the billing personnel. Further, the billing personnel would then have to translate the doctor's notes into codes that would be acceptable for insurance billing purposes, which would include codes to private insurance as well as codes to public insurance, such as Medicare. This required that the billing personnel became highly specialized in insurance procedures where the physicians or primary health care providers needed the services of such specialization in order to obtain payment from the insurance providers. If there was trouble with converting the real time medical records into appropriate insurance language, Then the health care organization would be delayed in obtaining revenue from the insurance sources to pay for the covered services.

Improved computerized data entry systems later came along that allowed a physician or health care provider to enter patient medical information during the examination, but that information still needed to be processed by the billing personnel prior to an accounting of services and costs could be given to the patient. It did speed up the recording of the medical records, but did not improve the actual billing and insurance collection process required by the doctors, the patients, and the insurance industry.

Billing code correlation later came along to correlate billing codes with planned or performed medical procedures. Raw codes were directly associated with all the medical procedures performed or planned to be performed with a particular patient examination and then the raw codes were manipulated in such a way as to generate intermediate codes that would later be used to determine the actual billing codes to be used in processing the billing reports to either the patient, the insurance provider, or both. Unfortunately, the billing code correlation approach focuses solely on the physician's Current Procedural Terminology (CPT) medical coding system of the American Medical Association (AMA) for reporting physician's services to the Medicare program. This approach also fails to provide for a real time accounting system that allows a doctor to view the actual costs associated with the services rendered in discussing these fees with the patient during the actual visit.

Accordingly, there is a need for a computerized medical records and billing system that allows for a doctor to view billing information on a real time basis with respect to the entry of services rendered at the time of the patient's actual visit. Furthermore, what is needed is a computerized billing system and medical records system that allows for a patient to consult with the doctor during the procedure to determine not only the best possible medical service for the patients needs, but also the most effective and cost efficient medical service for the patient's budget or means. Further still, what is needed is a medical records and billing system that allows a doctor to understand all phases of information entry into the data base that includes not only the patient information and treatment and diagnosis, but also the billing codes used for both private insurance and government insurances, such as Medicare. It is desirable that this system be offered in a useful manner that provides a graphical user interface to guide the health care provider and billing personnel through easy to understand steps that provide not only useful medical history records, but also clear and concise billing records for both the insurance industry and the patient.

SUMMARY OF THE INVENTION

According to the present invention, a record and billing service system and method are disclosed for use in health care offices. The system allows a user, typically a health care agent, to generate a visit form for a particular client. This form keeps a record of the patient's health history and treatment records received at that facility. The record includes vital statistics as well as information about the health care agent treating the patient. The records can be generated in a real time setting, meaning during the actual exam of the patient. The records are kept on a computer system and stored within a records data base for paperless storage. The system generates an application that shows the types of procedures, diagnosis, inventory, and the like normally provided in the health care office. The application can be customized to reflect specialties provided in that office. The system also converts the types of procedures, diagnosis and inventory matters listed in the application into accurate billing records. This provides the health care agent the ability to discuss the costs associated in the procedures and better structure a cost effective treatment or solution to the patient's needs. Further, the billing records are tied to conventional government and private insurance standards for easy billing and response. The system implements the application in a graphical user interface environment to facilitate the record keeping and report generation and printing.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention be described and explained with additional specificity and detail through the use of the accompanying drawings in which:

Figures 6, 7:
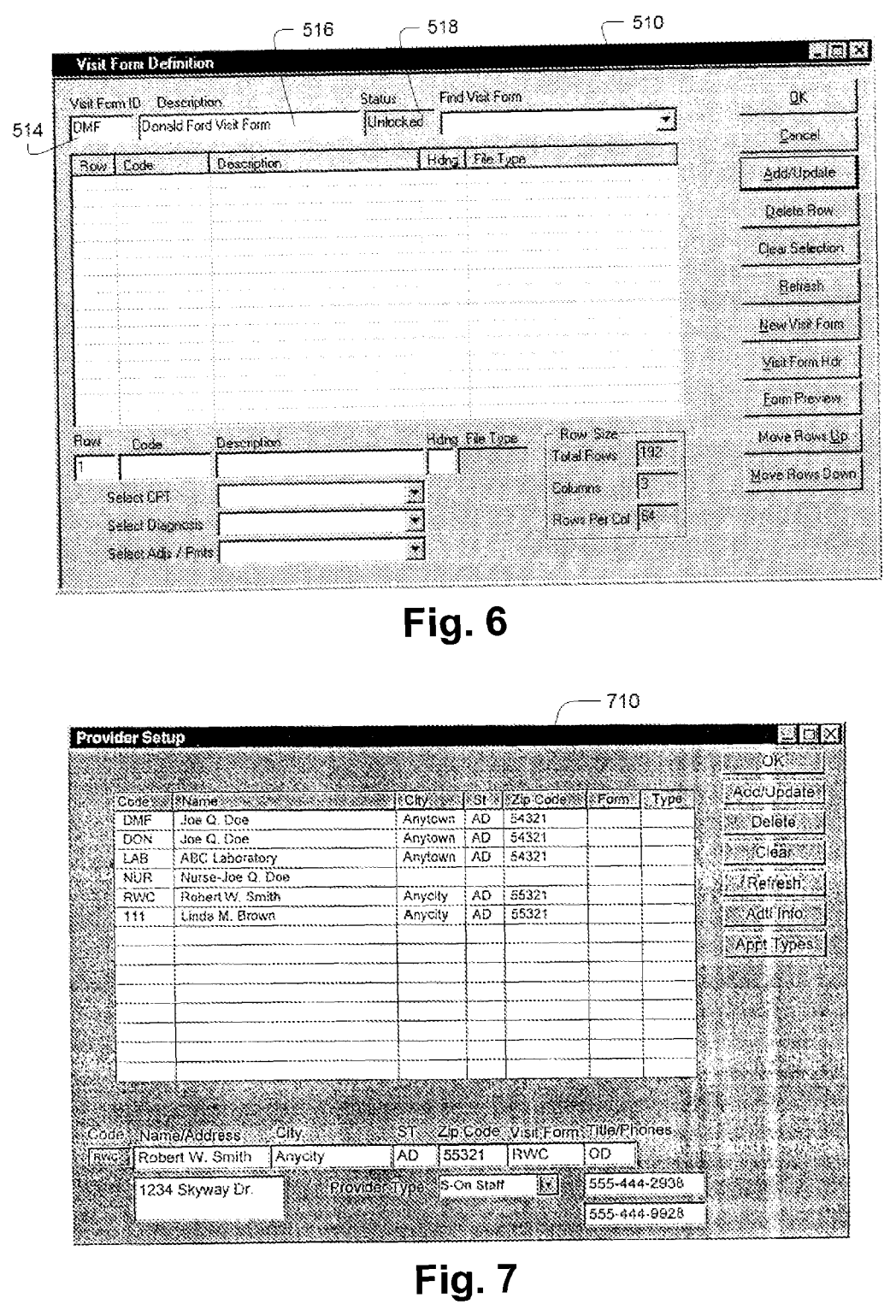

FIG. 6 is a second illustration of the interface of FIG. 5 where a patient definition is provided;

FIG. 7 illustrates an interface utilized by a user to define the health care agents, or providers, within the health care organization as seen by the patients;

Figure 12:
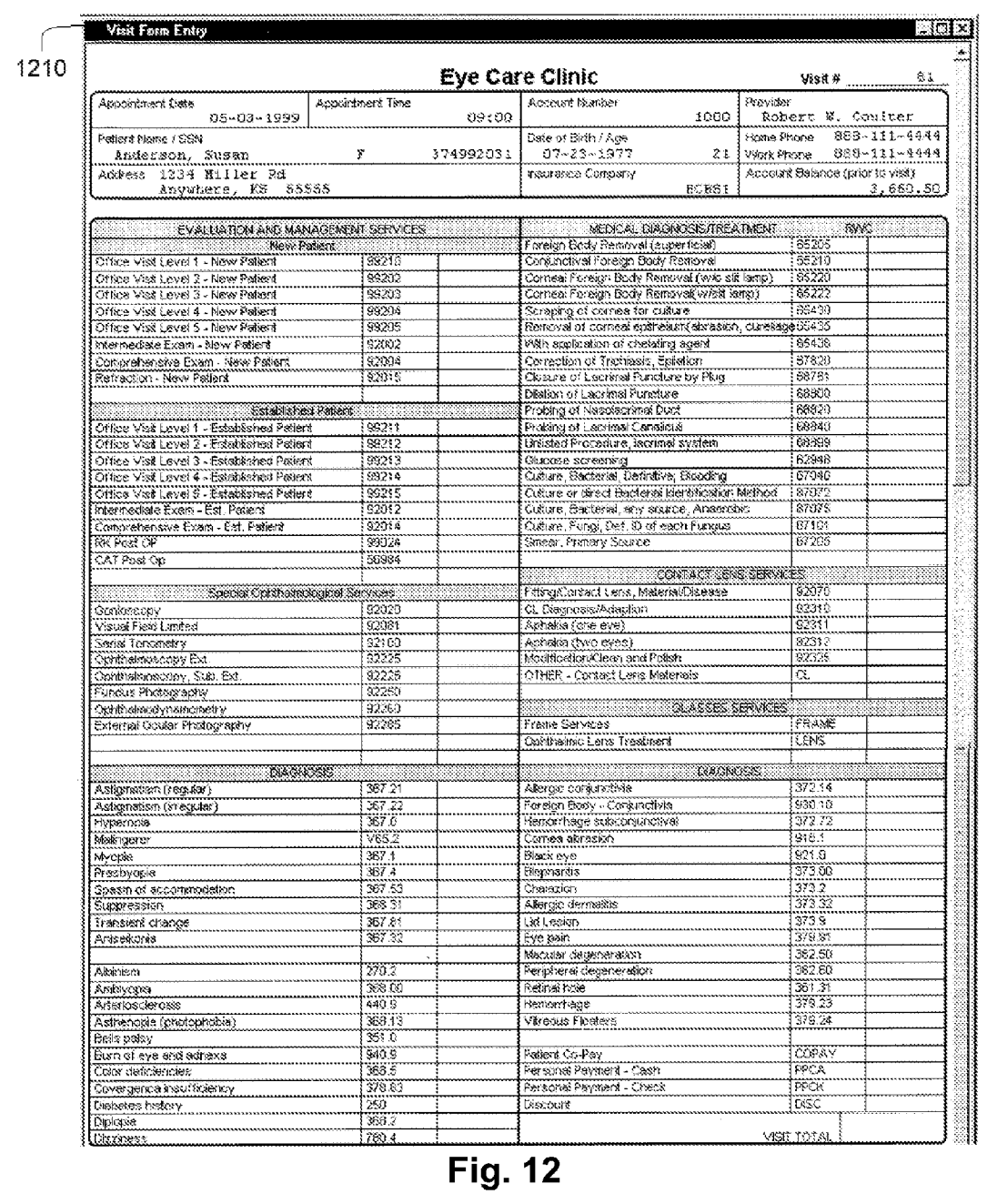

FIG. 12 is a visit form utilized by a user during a patient conference and diagnosis, as shown in interface form in accordance with the present invention;

FIG. 13 illustrates an inventory pull down menu feature of the visit form of FIG. 12;

FIG. 14 illustrates an interface utilized by a user to add a new account note to the visit form of FIG. 12;

FIG. 16 illustrates a record and billing summary printout for the patient after a visit with the health care agent.

DETAILED DESCRIPTION OF THE PREFERRED EMBODIMENTS

Figure 1:
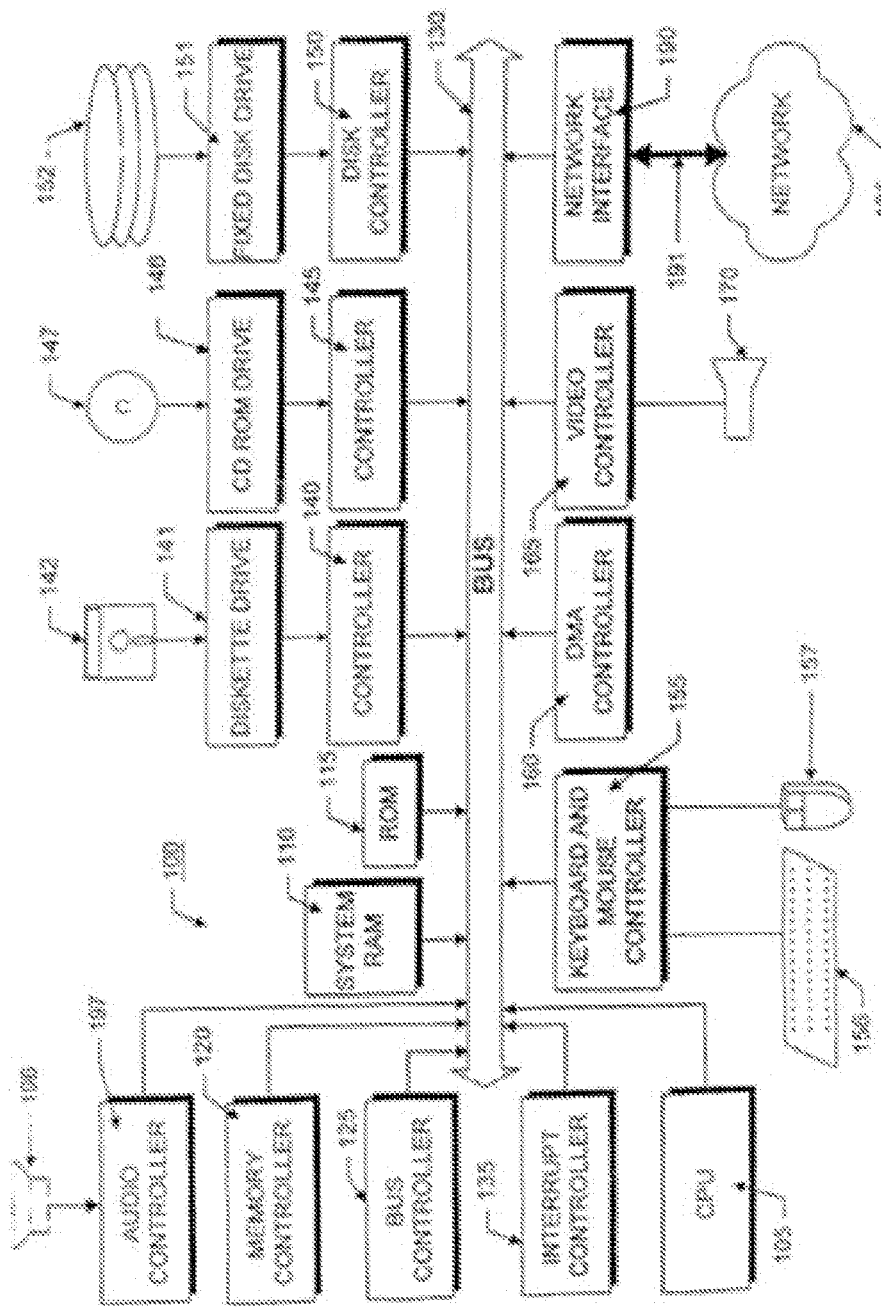
FIG. 1 illustrates a representative computer system upon which the present invention is implemented.

FIG. 1 illustrates the system architecture for a conventional computer system, such as an IBM Aptiva™ computer on which the inventive security system can operate. The exemplary computer system of FIG. 1 is for descriptive purposes only. Though the description below may refer to terms commonly used in describing particular computer systems, such as the IBM Aptiva computer, the description and concepts equally apply to other systems, including systems having architectures dissimilar to FIG. 1.

The exemplary computer 100 includes a central processing unit ("CPU") 105, which may include a conventional microprocessor; a system random access memory ("RAM") 110 for temporary storage of information and a read only memory ("ROM") 115 for permanent storage of information. A memory controller 120 is provided for controlling system RAM 110; a bus controller 125 is provided for controlling bus 130; and an interrupt controller 135 is used for receiving and processing various interrupt signals.

Mass storage may be provided by a diskette 142, a CD-ROM disk 147 or a hard disk 152. The diskette 142 can be inserted into a diskette drive 141, which is, in turn, connected to bus 130 by a controller 140. Similarly, the CD-ROM disk 147 can be inserted into a CD-ROM drive 146, which is also connected by a controller 145 to bus 130. Finally, hard disks 152 are part of a fixed disk drive 151, which is connected to bus 130 by controller 150.

Input and output to computer system 100 are provided by a number of devices. For example, a keyboard and mouse controller 155 connects to bus 130 for controlling a keyboard input device 156 and a mouse input device 157. A DMA controller 160 is provided for performing direct memory access to system RAM 110. A visual display is generated by a video controller 165, which controls a video output display 170. An audio controller 197 connects to bus 130 for controlling an audio output device 196. The computer also includes a communications adapter 190 which allows the system to be interconnected to a local area network (LAN) 195, a wide area network (WAN), as well as provide an Internet connect either directly, or via the LAN or WAN, which is schematically illustrated by bus 191.

The computer 100 is generally controlled and coordinated by operating system software, such as the Windows 98 or NT, or other compatible operating systems. In the Macintosh systems, the operating system confirms to 7.5.5 and higher. Workstation compatible systems typically use a UNIX or LINUX compatible operating system. Conventional operating systems-control and schedule computer processes for execution, perform memory management, provide file system, networking, and I/O services, and provide a user interface; such as a graphical user interface ("GUI"), among other things. User applications, such as editors, spread sheets, and internet browsers directly or indirectly rely on these and other capabilities of the operating system.

Figure 2:
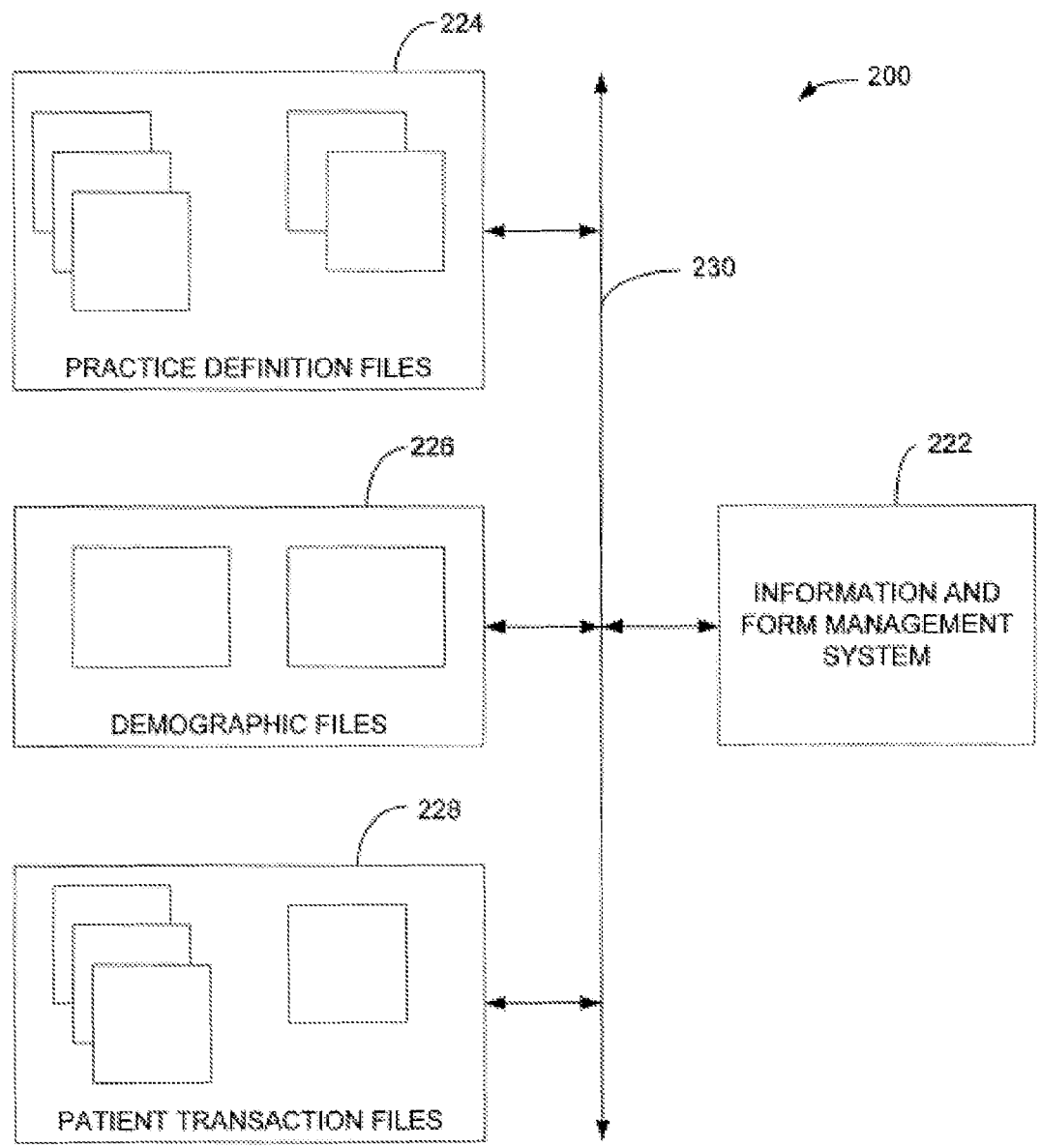
FIG. 2 is a block diagram of the database file and record management system in accordance with the present invention.

Computer 100 connects to a network 195, which provides access to an medical records and billing server database 200, which is shown in FIG. 2. Server database 200 is similar to computer 100 in hardware configuration and provides access to a multitude of instructional media to an end user at computer 100. Further, server database system 200 provides for recording a health care agent's visit with a patient. The health care agent in this application refers to any provider such as a doctor, nurse, medical assistant, dentist, dental assistant, among others. For example, the medical assistant receives a call from a patient. The medical assistant then sets up an appointment for the patient to see the doctor. The records show if the patient is a new or existing patient to that doctor or the health care office. The record further shows what treatment the patient has had in the past so the medical assistant can determine if the visit is for something the patient has been in for before or is something new. If the matter is something new, the records also show if it is time for any follow up visits for specific matters, such as dental or eye exams, pap smears, breast exams, and other routine preventative exams within the normal course of visiting.

Database system 200 further provides a means for storing file information relevant to the practice of a medical facility. This information, for this example, is illustrative of a medical practice, but alternative types of business arrangements, such as accounting firms, law offices, retail establishments, and the like, may amply benefit from information and management control system provided by database 200 in accordance with the present invention. Database system 200 further incorporates an information and form management system 222, which may essentially be a computer system such as that of FIG. 1 that allows a user to define the file types, file information to be stored, provide data entry into those particular files, and pull information from those files to generate the particular forms desired by the end user as provided in the present invention. For the purposes of an exemplary embodiment of the present invention, three different file types are provided for illustrative purposes. The first file type is that of practice definition files 224, which may be stored in long term, short term, or permanent memory locations for maintenance and manipulation. The second file type is that of demographic files 226. The third file type is that of patient transaction files 228. Information is transported from one file type to another and to other destinations by information and form management system 222 over bus 230.

When a user, such as a doctor, performs a service for a patient, the service is posted via database system 200. The system accesses any of files 224-228. Each type of file contains specific information relevant to either practice definitions, demographics, or patient transactions. For example, practice definition files 224 contain record sets that define how a practice works. These include provider definition records, provider appointment records, visit form definition, post definition records, such as, for example, CPT codes, adjustment codes, payment codes, text codes, and diagnosis code records. The provider definition records contain information about an individual provider. The provider appointment records further define how a provider works under different situations. For instance, a provider seeing a new patient, or a provider performing surgery, would perform different procedures, and therefore, have a different selection on the visit form. The visit form definition records define a pool of formats that can be selected by a provider to meet these individual needs. The posting definition records define the allowable codes the user may use in creating transactions. These transaction codes include the charge codes (CPT), adjustment codes, for example write-offs, discounts, and the like, and the payment codes, which include cash payment credit card payment, insurance payment, and the like. The diagnosis records define the medical reason a certain procedure (CPT) is used.

Demographic files 226 contain all information about an account and a patient necessary to generate statement and insurance forms. This information includes addresses, age, sex, marital status, insurance coverage, and other vital statistics related to the patient are contained in these records.

During an office visit, the provider meets with the patient. During this meeting, the provider accesses the definition records in the demographic files 226 to display or print a form for the provider to indicate what procedures have been performed on or behalf of that patient. After the provider or another office worker indicates those procedures that have been performed, or what adjustments and payments have been performed, transaction records are written into the database and stored in patient transaction files 228. The transaction files include charge, adjustment, and payment information as well as medical diagnosis information. These transaction records are later used in billing statement and insurance reimbursement form generation as is described in greater detail below.

All the records found within database 200 are used when any clinic personnel wish to view or print information about a patient's history. Since all the data is archived, the service provider can generate an exact image of the form or graphical user interface a screen that was initially used to recreate the session.

Figure 3A:
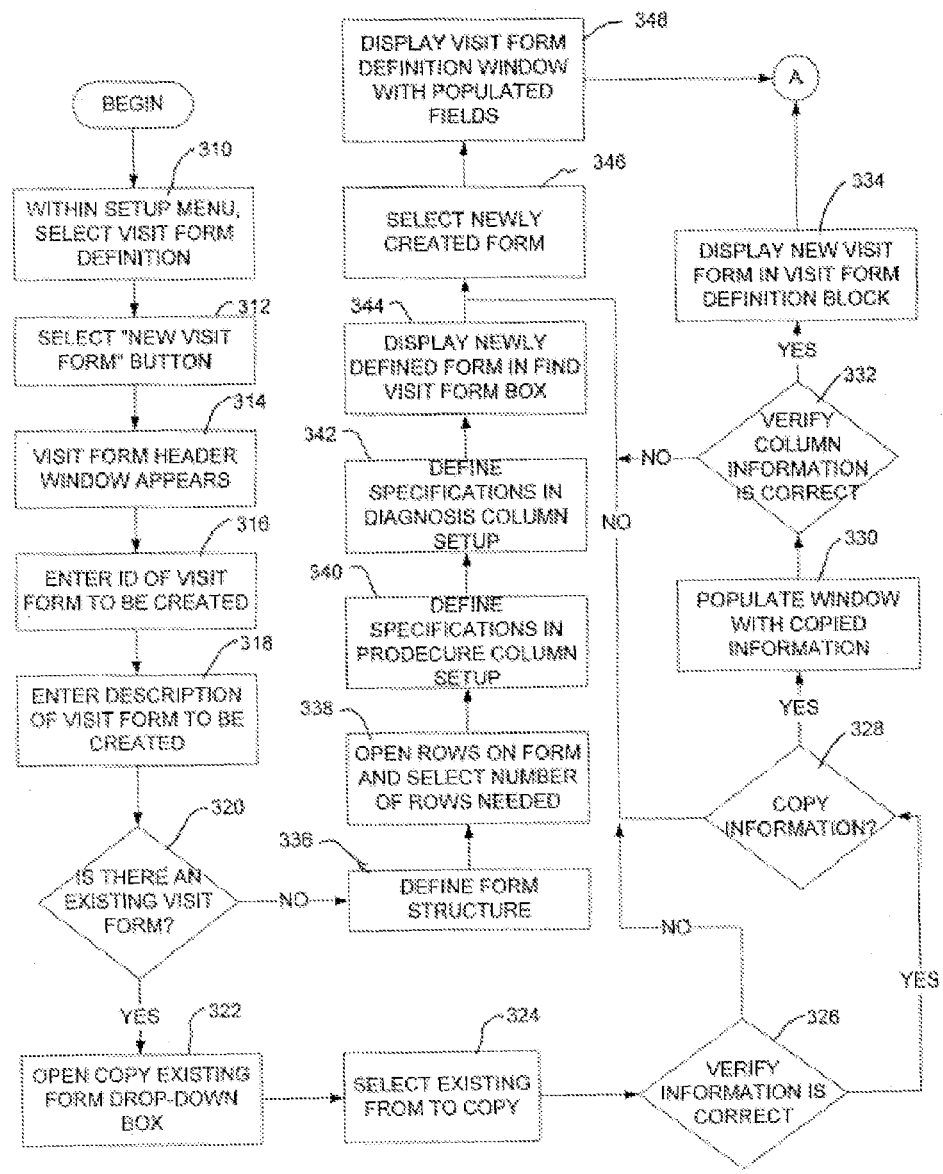
FIG. 3 is a flow diagram illustrating how a visit form is prepared in accordance with principles of the present invention.
Figure 3B:
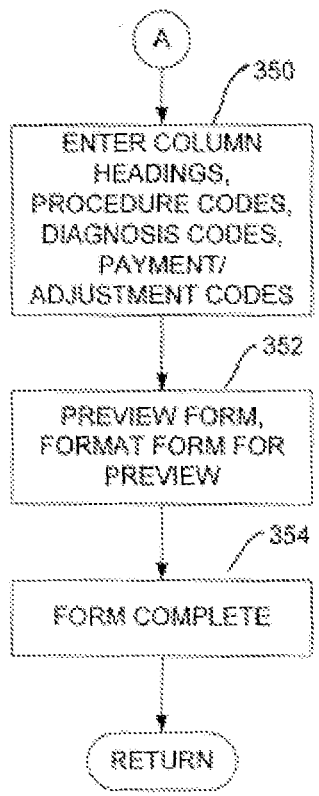
Figure 4A:
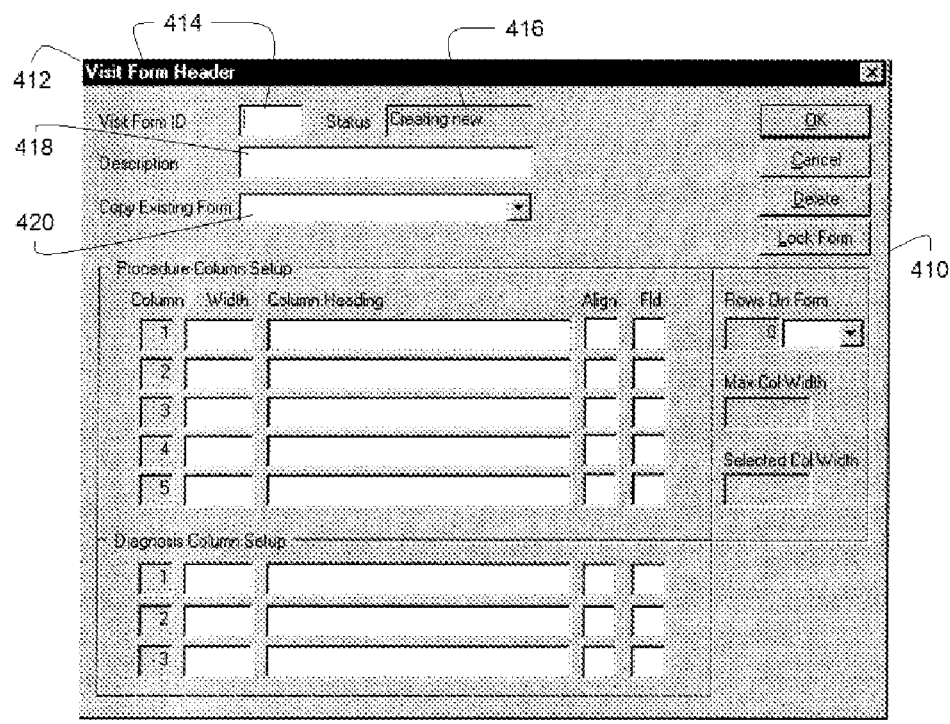
FIG. 4 illustrate the interface used by a user in generating a visit form in accordance with FIG. 3.
Figure 4B:
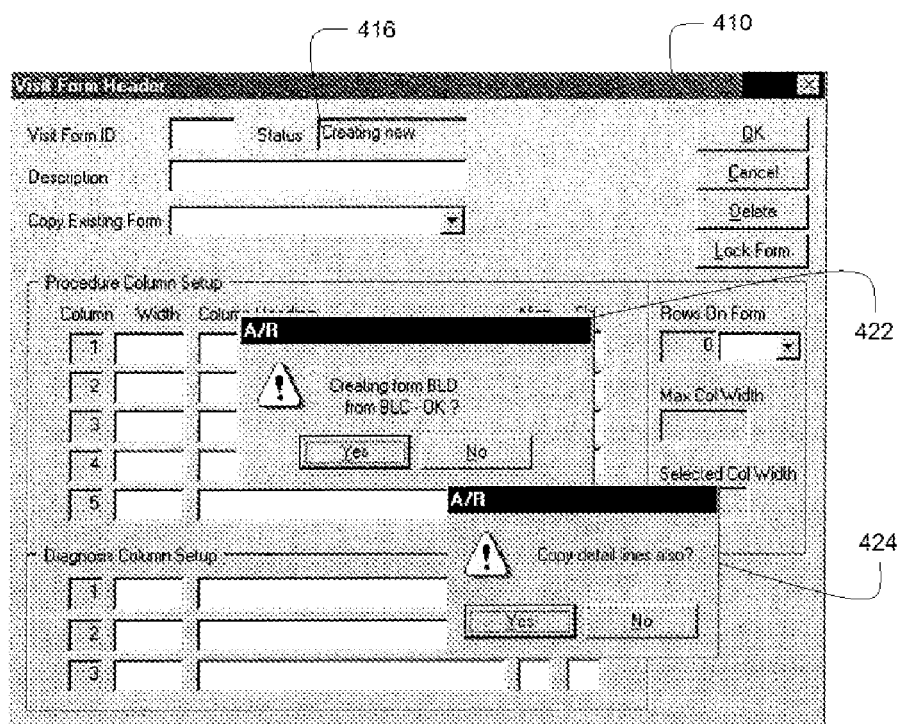
Figure 4C:
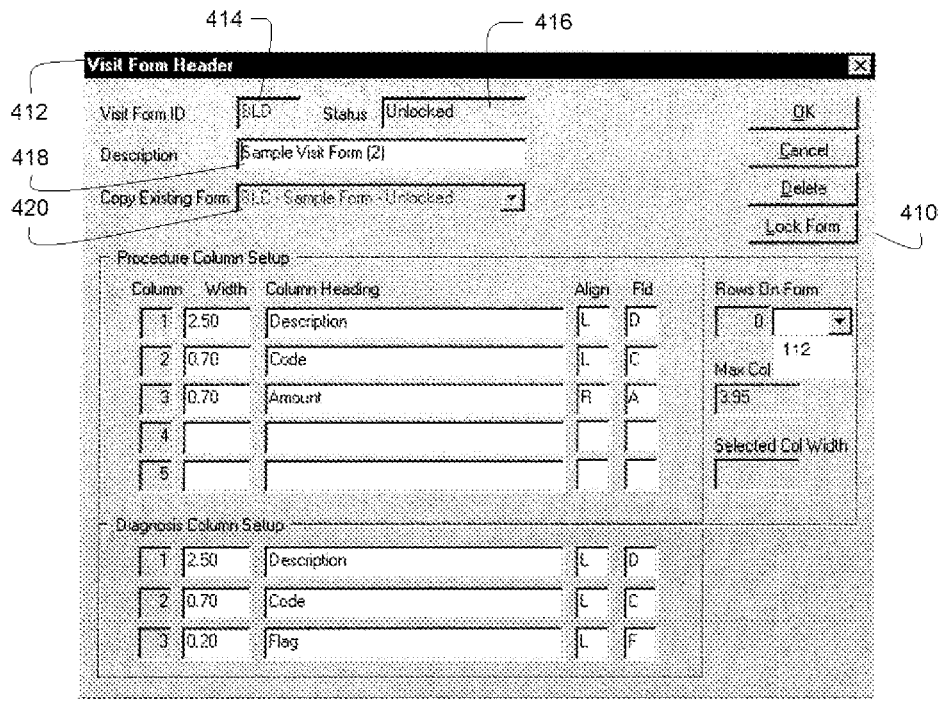
Figure 5:
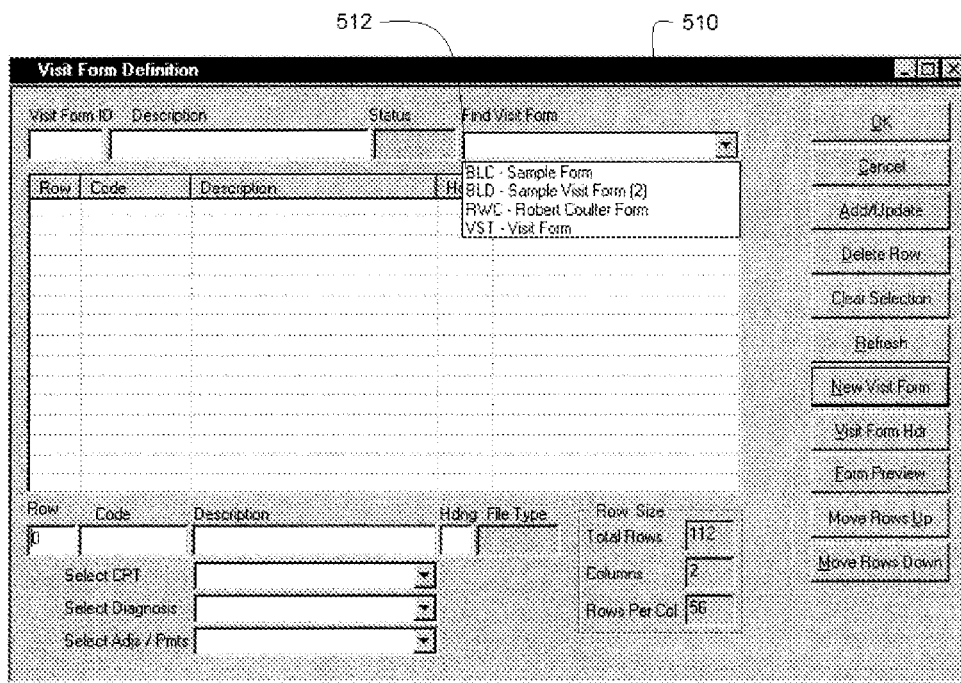
FIG. 5 illustrates an interface utilized by a user to define aspects of the visit form in accordance with principles of the present invention.
Figures 8, 11:
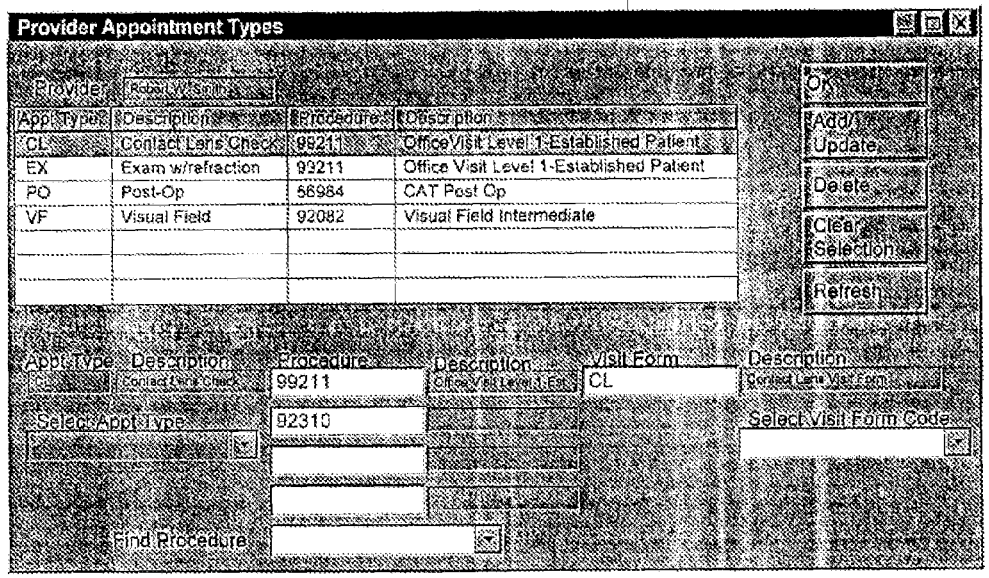
FIG. 8 illustrates an interface utilized by a user to define the appointment types offered within the health care center.
FIG. 11 illustrates an interface utilized by a user in defining a new appointment for a patient.

In accordance with the present invention, a method and system for storing patient medical information is disclosed. The medical information includes who the patient is, the patient's prior treatment, known allergies, and other medical information typically surveyed from the patient or garnered from prior medical treatment at scheduled appointment is to commence. An example of a typical visit form in accordance with the principles of the present invention is illustrated in FIG. 12, which is described in greater detail below. The first section disclosing the present invention is directed towards the actual setting up of a visit form for use in a specific health care facility. Such health care facilities can be selected from general practice medicine to specialties such as orthopedics, opthalmology, dentistry among others. FIGS. 4-6 along with the flow diagram of FIG. 3 present the set-up of the actual visit form to be used within a particular-health care-organization. For this example, the health care organization is an eye care center. The second section of this disclosure is directed towards the development of visit forms as defined by appointment types of specific providers within the health care organization. This is illustrated in FIGS. 7 and 8 and described in the flow diagram of FIG. 9. Lastly, the third section of the present invention discloses how a visit form is utilized within the method and system for recording the medical information of a given patient and then providing comprehensive billing record of the same. FIGS. 11-16 illustrate the various stages of actually completing a visit form and then generating a transaction history for a given patient account and is described with respect to the flow chart of FIG. 10.

Establishing a Visit Form

FIG. 3 depicts a block diagram of a flow chart detailing the steps performed in establishing a Visit Form, like the one shown in FIG. 12, for use in recording medical information and history of a patient within a medical organization, health care facility, dental office, or surgical center, but not limited thereto. The form developer, also referred to as the system user, interfaces with the form generation program in accordance with the present invention within a graphical user interface (GUI) a illustrated in FIGS. 4-6. FIG. 4A depicts a GUI screen of a visit form field 410 in accordance with the present invention. Visit Form field 410 is noted by a header 412 defined as "Visit Form Header." A Visit Form ID 414 is provided as well as a Status box 416. A Description 418 for the Visit Form Header is provided in addition to a Copy Existing Form box 420. Additional elements are provided that are standard within a GUI screen such as the following activation buttons "OK," "Cancel," "Delete," and "Lock Form."

Visit forms are used to record the procedures performed and diagnosis given a patient while visiting with a health care agent. The visit forms may be printed to provide the patient with a record.

To establish and define a given visit form, the user selects a "Visit Form Definition" operation within a given set-up menu as shown in step 310. Next, in step 312, the user selects a "New Visit Form" button and a Visit Form Header window 410 is displayed at this point as shown in step 314. Next, in step 316, the user enters a Visit Form ID in field 414 to identify the visit form being created. Next, in step 318, the user enters a description of the visit form being created in Description field 418.

If there is an existing visit form, as inquired in step 320, and the existing visit form has the same format or much of the same data needed for the new form, the user selects the form and the system proceeds to step 322. Otherwise, the system proceeds to step 336. Thus, if there is no existing form, a new form structure must be defined using the remainder of the window as provided in steps 336-344. Continuing to step 322, the user opens a copy of the existing form by way of the drop-down box in field 420. Next, in step 324, the user selects an existing form to copy. This is verified by the user by selecting the "Creating form BLD from BLC-OK" warning block 422 shown in FIG. 4B. Once the information is copied, the user then asked to verify if the information displayed is correct as shown in step 326. If the information is correct, the system continues to step 328 where the information is actually copied; otherwise, the system proceeds to step 346.

In step 328, the user is again asked to confirm whether the information needs to be copied via "Copy Detail Lines Also" warning block 424. If the user elects to copy the information, then the system proceeds to step 330; otherwise, the system proceeds to step 346. In step 330, the system begins populating the window with the copied information. FIG. 4C illustrates the Visit Form window 410 being repopulated in response to step 330.

In the example of FIG. 4C, the Visit Form ID is identified as "BLD," which are the initials of the provider's name. Status field 416 is unlocked and Description field 418 is provided with a Sample Visit Form (2). Copy Existing Form field 420 now includes a BLC-Sample Form-Unlocked describing from which sample form Visit Form ID BLD originated. Information pulled from the BLC sample form is used to populate the procedure column set-up and diagnosis column set-up as shown. Three different columns are populated in the procedure column set-up with a column heading for each including "description," "code," and "amount." Within the diagnosis column set-up, there are three columns as well and their descriptions include "description," "code," and "flag."

A typical visit form is designed to be printed on an 8½ by 11 inch form, but other sizes may be used, such as A4, legal size, or 8½ by 14 inch, or any other paper size desired by the medical facility. The procedure column set-up and diagnosis column set-ups can be defined to have a desired column width and sequence. These widths are adjustable according to the needs of the user based on the user's personal taste and functional arrangement of the actual visit form. After the Visit Form Header window 410 has repopulated with the copied information, the system then verifies that all column headings, widths, alignment, and field type are correct as shown in step 332. If the column information is not correct the system proceeds to step 346; otherwise the system proceeds to step 334.

In step 334, the system displays the new visit form in a Visit Form Definition window 510 illustrated in FIG. 5. At this point, the original Visit Form Header window 410 of FIG. 4 disappears and the newly generated Visit Form BLD-Sample Form appears in the Find Visit Form drop-down box 512 of the Visit Form Definition window 510. At this point, the system proceeds to FIG. 3B to continue from flow connector A and complete steps 350-354.

Returning to step 320, if there is no existing visit form to select, the system then proceeds to step 336. In step 336, the system defines the form structure as selected by the user, which in this case is illustrated by the Status window 416 as "Creating New" shown in FIG. 4A. Next, proceeding to step 338, the system opens the Rows On Form field for the user to select the number of rows needed. After the user selects the desired number of rows, the system proceeds to step 340 where the user is allowed to define the specifications in the Procedure Column Setup field shown in Visit Form Header window 410. After defining the specifications for the procedure column(s), the system proceeds to step 342 where the user defines the specifications in the diagnosis column setup as provided in the Diagnosis Column Setup field of window 410. After the specifications for both the diagnosis and procedure columns have been defined, the system then displays the newly defined form in FIG. 5 further in Find Visit Form box 512, in accordance with step 344.

In setting up the Procedure Column Setup section of window 410, the user defines the specifications for each of the columns by entering the width of each column, entering the heading to appear over each column, defining the alignment box, and defining the field box. In the alignment box, a C, L, or R is used to either center the data within the column, perform left justification, or perform right justification of the data, respectively. In the FLD or, field box the user enters either a C, D, or A, which is used to define if the data to be entered is the procedure code, the procedure description, or the procedure amount, respectively. Alternatively, the FLD box may be left blank if the data is something other than a code, description, or amount.

In the Diagnosis Column Setup section of window 410, the user defines the specifications for each of the columns by entering the width of each column, entering the heading to appear over each column, and defining the align box and field box in the same manner as was done with the Procedure Column Setup previously described.

As depicted in step 346, the user selects the newly created form in the Find Visit Form drop-down box 512 shown in FIG. 5. Once the appropriate visit form is selected, the system displays the visit form definition window 510 with the populated fields from the created form in accordance with step 348. Next, the system proceeds to step 350 shown in FIG. 3B.

FIG. 6 depicts a Visit Form Definition window 510 like that in FIG. 5 as selected in either step 334 or 348. In this example, visit form ID field 514 provides an identification of the patient by way of the provider's visit form ID. Other types of identifiers may be used, such as, for example, specialty practice, hospital designation, or other identifier related to the patient by procedure, provider, location, or the like. In this example, the provider's name is Donald Ford with the initials being DMF. A description of the actual form is shown in Description field 516, which in this case is Donald Ford Visit Form. The status shown in Status field 518 is "unlocked." From here, the user enters and defines column headings, procedure codes, diagnosis codes, and payment/adjustment codes as shown in step 350. To enter column headings, the user first verifies that their own number is correct and then skips the actual code billed. Next, the user enters the wording for the heading in the description field. Descriptions may include, for example, the following:

Procedures
Procedures Evaluation and Management Services
Contact Lens Materials

Next, the user enters a "Y" in the HDNG box located next to the description field and then presses <enter>.

A user can enter procedure codes in one of two ways. The first manner in which user can enter procedure codes includes verifying that the row number is correct, opening the Select CPT drop-down box, searching for the appropriate CPT code desired by either using the scroll bar on the right of the drop-down box or by entering the first characters of the CPT code to position the entries closer to the desired code, click on the desired CPT code, and then press <enter>. The second way for entering a procedure code is to verify that their own number code is correct, enter the CPT code in the Code field, enter the CPT description in the Description field, and then <enter>. Next, the user enters a desired diagnosis code.

There are two ways in which the diagnosis codes may be provided. The first way is performed as follows. Initially, the user verifies that their own number is correct, then the user opens the Selected Diagnosis drop-down box shown within the Select Diagnosis drop-down box field, then the user searches for the diagnosis code desired by either using the scroll bar to the right of the drop-down box or by entering the first characters of the diagnosis code to position the entries closer to the desired code. Once the desired code is selected, the user clicks on that code and presses enter to effect the selection. The second way in which the user may select a desired diagnosis code is to first verify that their own number is correct, enter the diagnosis code in the code field, enter the diagnosis description in the description field, and then press enter.

Lastly, the user enters the payment/adjustment codes by one of two ways. Initially, the user verifies that their own number is correct, opens the Select Adjs/Pmt drop-down box, searches for the Adjust or Payment code prescribed in a manner similar to that described for other drop-down box interfaces, clicks on the desired adjustment payment code and presses <enter>. The second manner includes verifying that their own number is correct, as in the first manner, entering the payment or adjustment code in the code field, entering the payment or adjustment description in the Description field, and then pressing <enter>.

Next, as shown in step 352, the user clicks on the Form Preview button within the Visit Form Definition window 510 of FIG. 6. Upon selecting the Form Preview button, the system then formats the form for review by the user to verify that the selections made with respect to headings, procedure codes, diagnosis codes, and payment/adjustment codes has been properly effected. Once the form is complete as shown in step 354, the user clicks OK and exits the Visit Form Definition window 510.

Provider and Appointment Form Setup

Figure 9:
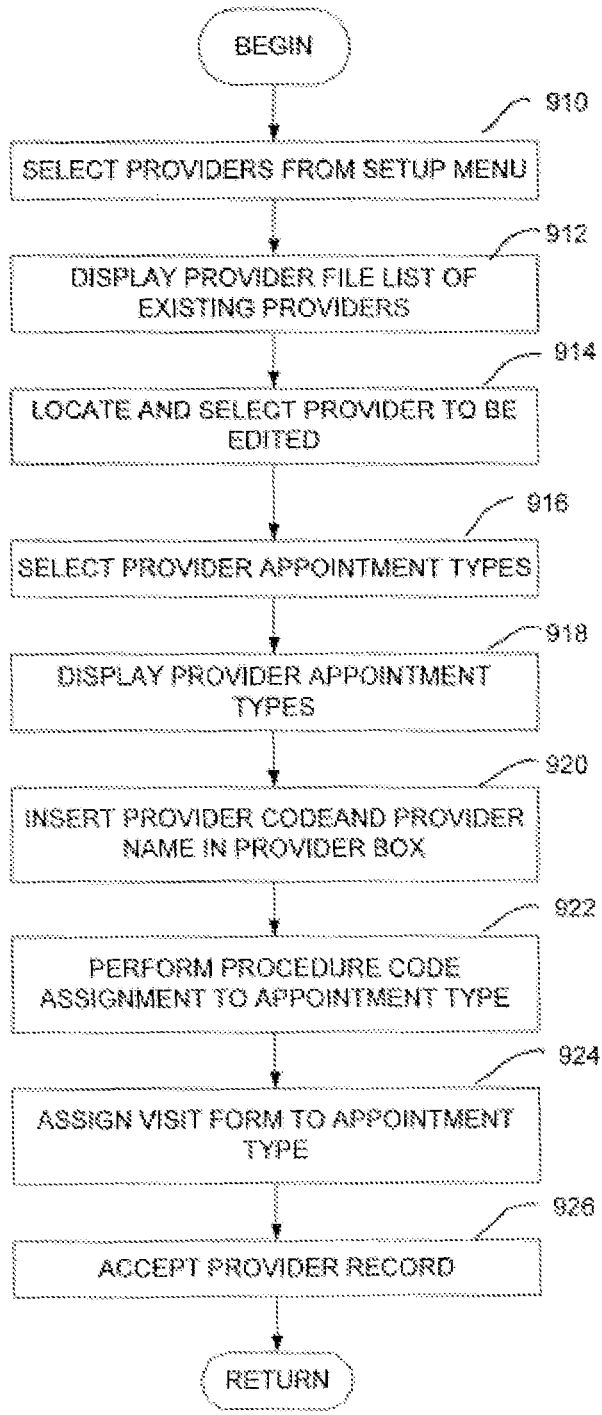
FIG. 9 is a flow diagram depicting the method and operation of defining the providers and appointment types within the health care center, as prescribed by the present invention.

This section discloses the development of visit forms by appointment type and by provider as illustrated in FIGS. 7 and 8 and the flow diagram illustrated in FIG. 9.

First, the user selects a provider for the particular appointment type and visit. At this stage, the selected provider and appointment type can list several options that are typically associated with the particular appointment type. Upon selection, the user defaults to the listed options, unless the user deselects these options prior to finalizing the visit and appointment type entry related to the patient. To select the providers for the appointment types and visit forms, the user selects the providers from a set of menu as shown in step 910 in the flow diagram of FIG. 9. In step 912, the system displays a provider file list of the existing providers as shown in Provider Setup window 710 of FIG. 7. Once the provider file list is displayed, the user locates and selects a provider to be edited in accordance with the step 914. Next, in step 916, the user selects the provider appointment types as noted by the APPT Types button in window 710. The system displays the provider appointment types as shown in FIG. 8 in Provider Appointment Types window 810. At this point, the system automatically inserts the provider code and provider name in the appropriate Provider field shown in FIG. 8 in accordance with step 920. The use is now allowed to make modifications such as additions or changes to the provider shown in the Provider field of FIG. 8.

Next, in step 922, the user performs a procedure code assignment to a given appointment type. This is performed in one of two ways. The user can assign one or more procedure codes to an appointment type by manually entering a valid appointment type code in the APPT Type box, tabbing to the first procedure field immediately to the right of the appointment type description, manually entering a valid procedure, or posting code in the first procedure box where in this example as many as five procedure codes may be assigned to an appointment type by manually entering the valid procedure codes in the subsequent procedure fields. Alternatively, the user can assign one or more procedure codes to an appointment type by opening the select appointment type drop box shown within field 810 and clicking on the appointment type to assign and then opening the find procedure drop box and clicking on the procedure code to assign.

Once the procedure codes have been assigned to the appropriate appointment type, the system proceeds to step 924 where the user assigns the visit form to the appropriate appointment type. There are two options for assigning a visit form to an appointment type. The first option allows the user to enter manually a valid appointment type code in the APPT Type box, tab to the appropriate visit form field immediately to the right of the procedure-description column, and manually enter a valid visit form code in the visit form box. The second option allows the user to open the Select Appointment Type drop-down box and click on the appointment type to assign and then open the select visit form code drop-down box and click on the visit form to assign. Afterwards, the user verifies that the proper assignments have been made and the system accepts the provider record in accordance with step 926. This is done by clicking on the OK button shown in Provider Appointment Types window 810. The provider appointment types are now completed and the system returns for further processing.

Patient Profile and Billing Record

Figure 10A:
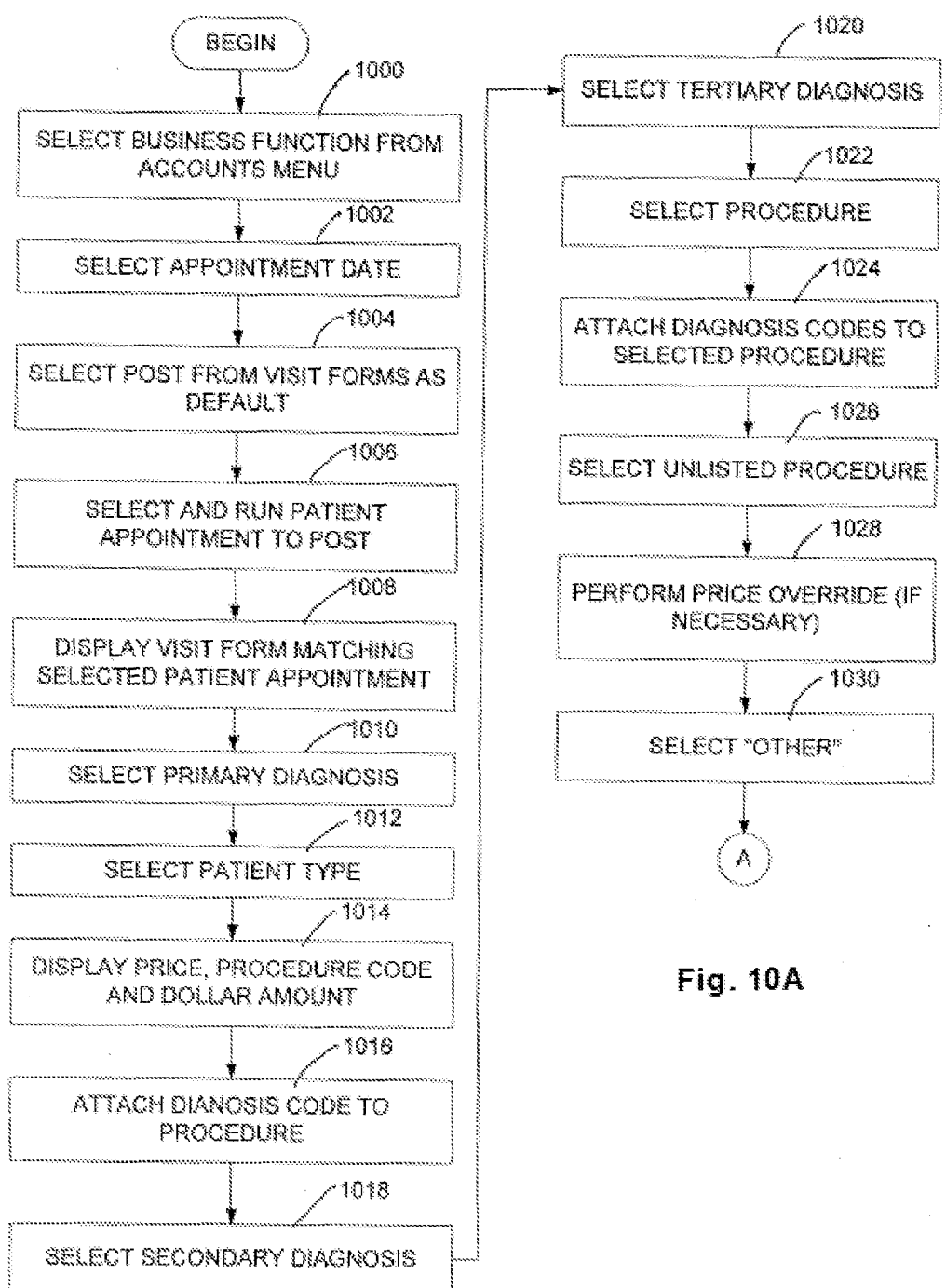
FIG. 10 is a flow diagram depicting the generation of a final visit form of an actual visit of a patient, in accordance with the present invention.
Figure 10B:
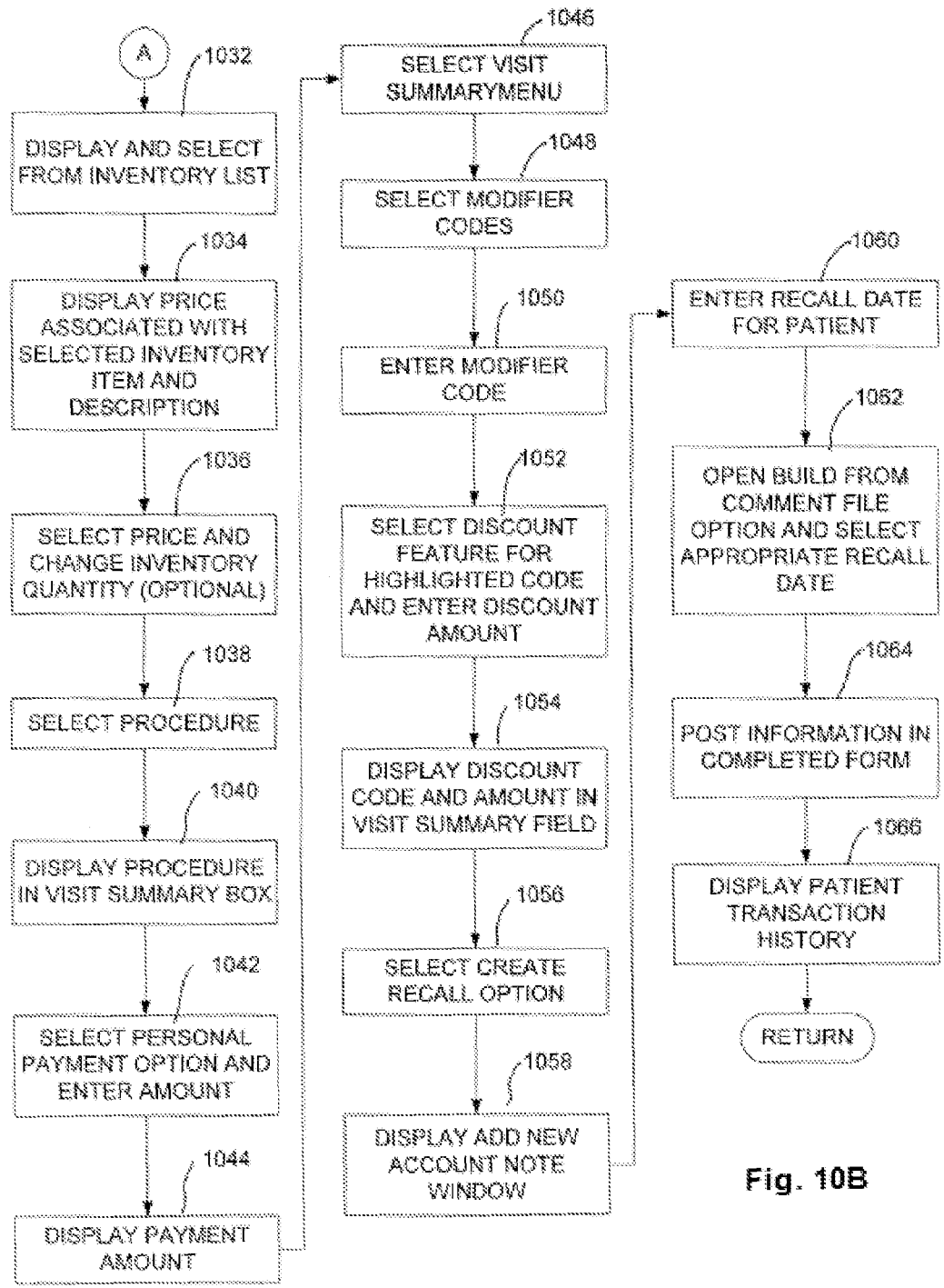

FIG. 10 is a flow diagram of the implementation of a patient profile and billing record in accordance with principles of the present invention. The patient profile provides for medical records that a physician or medical care attendant can review when visiting with the patient during future visits. The billing records allow for the medical service attendant to view the status of the bills incurred during the services rendered to the patient so that the patient can see the cost as well as being able to pay either personally, via insurance, or by some other means.

The user, meaning the health care agent, begins in step 1000 by selecting a business function selection from the accounts menu that has been described previously. Once the business function has been selected, the program displays Business Functions window 1110 as depicted in FIG. 11. Window 1110 includes a Calendar section 1112 for selecting any day upon which visits are to be scheduled or have been scheduled. When the Business Functions window 1110 is displayed the appointments for the current date automatically appear as established by the computer system. If appointments for a different date or for multiple dates are desired, the user selects the appropriate appointment date in accordance with step 1002, which allows the user also to select a range of dates by clicking and holding a beginning date and moving to the ending date-before releasing. At this point, as shown in step 1004, the user verifies that the post from visit forms radio button is selected, which is typically set by default. In step 1006, the user selects and runs the patient appointments to post by clicking on the run button within window 1110. At this point, as shown in step 1008, the system then displays a visit form matching the select patient information where the patient information is automatically populated in the appropriate fields as shown in FIG. 12.

FIG. 12 illustrates a Visit Form Entry window 1210, in this example for an Eye Care Clinic. There is a Visit # field as well as fields for appointment date, appointment time, account number, provider name, patient name and social security number, date of birth, phone numbers, addresses, insurance company, and account balance. Additional fields include evaluation and management services, medical diagnosis and treatment, which both have additional subsets as illustrated in FIG. 12. Next, in accordance with step 1010, the user selects a primary diagnosis. The user makes this diagnosis selection by selecting one of the Diagnosis field of window 1210. If a desired diagnosis is not visible, the user then can scroll down using the scroll tools shown on the right side of window 1210 until the user locates the desired diagnosis. At this point, the user selects the diagnosis by placing a check mark next to it. Upon selection of the given diagnosis, a price associated with that diagnosis is automatically entered into the accounting portion of the program, which displays the price on the procedure line adjacent the selective diagnosis. Further, the procedure code and dollar amount is then inserted in the visit summary box 1520 of FIG. 15. Next, in step 1012, the user selects the patient type, and in response to the selection, as shown in step 1014, the system displays the price, procedure code, and dollar amount as previously described in the visit summary box. Significantly, the diagnosis code is attached to the procedure as shown in step 1016.

In step 1018, the user then is able to select a secondary diagnosis and any subsequent diagnosis, where applicable, by clicking on the appropriate diagnosis shown on the field of view. Next, in step 1020, the user, if applicable, selects a tertiary diagnosis. Next, in step 1022, the user selects an appropriate procedure and the appropriate and selected diagnosis codes are then attached to the selected procedure as shown in step 1024. The system provides the option for the user to select an unlisted procedure, as shown in step 1026. When the user selects an unlisted procedure, an Enter Amount box is generated and displayed to override any predefined price. Step 1028 illustrates that the user, not only when selecting an unlisted procedure, may perform a price override when necessary. Further, there is an "Other" selection where the user selects "Other" as shown in step 1030.

Figures 13, 14:
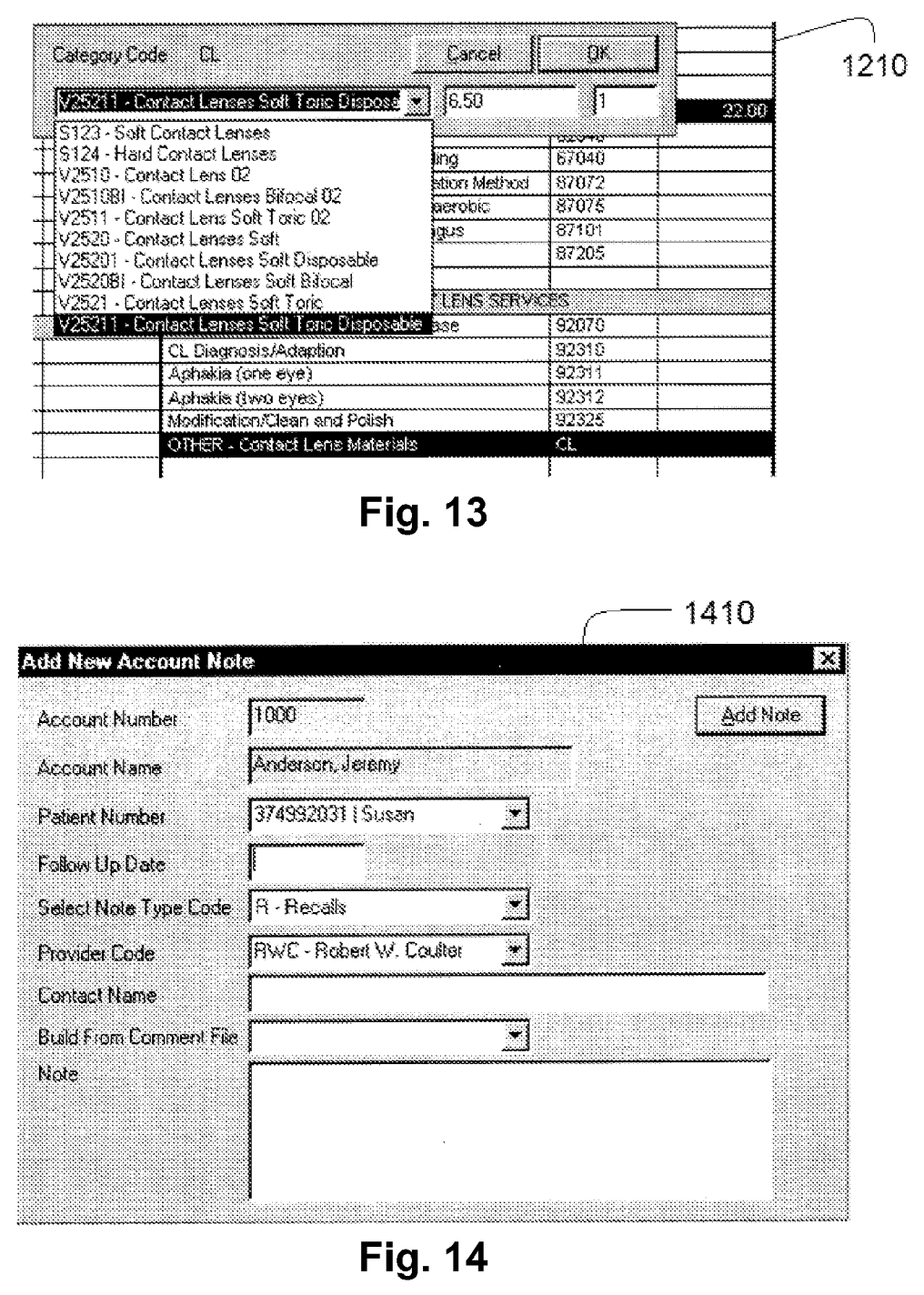
Figure 15:
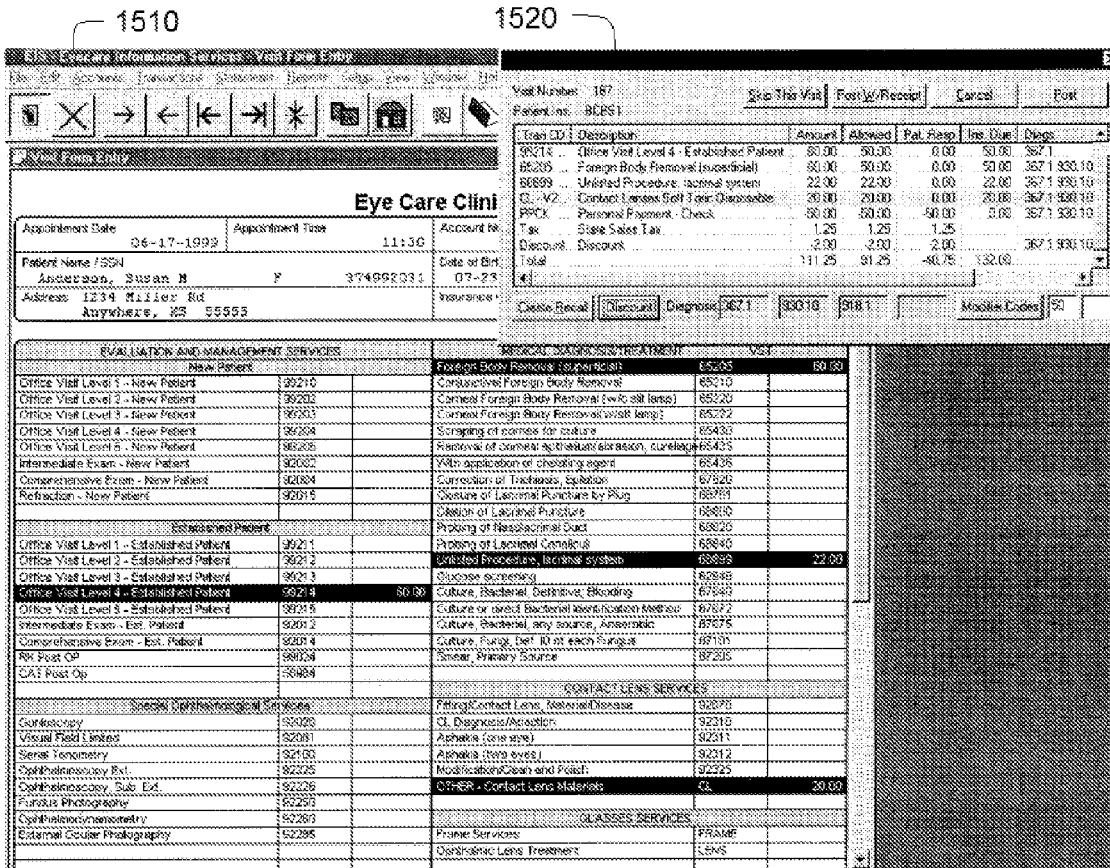
FIG. 15 illustrates an Office Visit Summary feature of the visit form of FIG. 12 as utilized by the user during a office visit by a patient.

In this example, which is also illustrated in FIG. 13 that is a window close-up view of field 1210 of FIG. 12, a drop-down menu for category code is depicted. This example uses the codes for contact lenses. This procedure in this example is made up of inventory, so a list of associated inventory items is displayed. The user then selects the desired inventory item, in this case "Contact tenses Soft Toric Disposable," and then the associated price appears in the box next to the inventory code and description. The user can change the price by using the price override feature as previously described. Further, the user can change the quantity of items from one to two or more. The system then displays the appropriate inventory list as shown in step 1030 while allowing the user to select from the inventory list displayed Next, in step 1032, the system displays the price associated with this selected inventory item along with an appropriate description. Then, in step 1034, the user can select the given price and change the inventory quantity as an optional step. Once the selected price and quantity of inventory has been selected, the user clicks OK. At this point, as shown in step 1036, the system enters the procedure in the Visit Summary box 1520, which is illustrated in FIG. 15 and as performed in step 1038. Further, the user can deselect a given procedure, which has the effect of removing that procedure from the visit summary box and the totals are adjusted accordingly in an automatic fashion.

Once the visit has been completed and all the services and diagnoses and procedures have been entered, the user, with the aid of the patient, selects the personal payment option and enters the final amount in accordance with step 1040. This amount is then displayed as the payment amount made by the patient and as shown in step 1042. Once the amount has been properly entered as that being paid by the patient, the amount is displayed along with the payment code in Visit Summary box 1520. The user next can select the Visit Summary window to perform a modifier code option. Modifier codes allow the provider to modify the procedure to reflect the actual service rendered, which may be either more or less than what was initially selected. For example, in some cases, the review may be routine enough that a full visit is not performed, hence a discount would be in order. In another example, during a surgical procedure, the surgeon may discover other complications not previously know and modify the service accordingly so that the insurance billings will reflect the discovered complications. The user selects the Visit Summary menu in accordance with step 1044 and then selects the modifier codes in accordance with step 1046. In step 1048, the user enters a desired modifier code, for example the user can enter a bilateral procedure code to a highlighted code shown in the visit summary box. These modifier codes can include such modifications as a discount code, activated by a discount button as shown in FIG. 15 in eye care information services—visit form entry window 1510 and in pull-down window or visit summary window 1520 where a discount button is provided. Step 1050 illustrates that the user can select the discount feature for the highlighted codes and enter the appropriate discount amount. The following which, in step 1052, the system displays the discount code and amount in the visit summary field.

Next, in step 1054, the user can select a Create/Recall button shown in the visit form field 1210, which displays an Add New Account Note window in accordance with step 1056 and illustrated in the window 1410 of FIG. 14. In step 1058, the user enters the recall date for the patient. This recall date is utilized to set up a time for the patient to return for a follow-up visit or a scheduled routine visit at the health care office. Next, in step 1060, the user opens the Build From Comment File drop-down box, selects the Add Note button so that the recall can be added. Then, in step 1062, the user clicks on the Post button, which can also post with receipt, to post the information in the completed form, process the entered visit information, and generate a receipt. Once this is completed, the system displays the patient transactions history in step 1064, which is illustrated in the Transaction History diagram 1610 shown in FIG. 16. In this example, for the eye care clinic, a transaction history for the account 1000 is displayed. The name of the patient is listed, the code description for the transactions along with the amount are displayed with a subtotal for the period of the transaction as well as a current account total due being displayed for the benefit of the health care facility and for the patient.

In another alternative embodiment, the invention may be implemented as a computer program product for use with a computer: system. Such implementation may include a series of computer instructions fixed either on a tangible medium, such as a computer readable media (e.g. diskette 142, CD-ROM 147, ROM 115, or fixed disk 152 as shown in FIG. 3) or transmittable to a computer system, via a modem or other interface device, such as communications adapter 190 connected to the network 195 over a medium 191. Medium 191 may be either a tangible medium (e.g., optical or analog communications lines) or a medium implemented with wireless techniques (e.g., microwave, infrared or other transmission techniques). The series of computer instructions embodies all or part of the functionality previously described herein with respect to the invention. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable media with accompanying printed or electronic documentation (e.g., shrink wrapped software), preloaded with a computer system (e.g., on system ROM or fixed disk), or distributed from a server or electronic bulletin board over a network (e.g., the Internet or World Wide Web).

The present invention may be embodied in other specific forms without departing from its spirit or essential characteristics. The described embodiments are to be considered in all respects only as illustrated and not restrictive. For example, although the specific embodiments have been limited to application in the medical services industry, the invention has broader applications in that it is directed towards and covers those situations wherein accounting, reporting, and billing records are coordinated during client/patient/customer meetings. This can include insurance companies that have insured clients meet during an office visit to review policies, values, claims and the like. It also can include law offices where billing programs lack this real time ability to provide a services accounting and billing statement in a quick and easy fashion by the legal services provides, typically an attorney, without the need to "go through accounting" first. The scope of the invention is, therefore, indicated by the appended claims rather than by the foregoing description. All changes which come within the meaning and range of equivalency of the claims are to be embraced within their scope.

What is claimed is:

1. In a system that is configured to be associated with healthcare services, a method for generating, displaying and recording healthcare service information, the method comprising:

electronically selecting a pool of healthcare procedures characteristically performed by an individual healthcare provider of a healthcare facility for inclusion in a customized form for use by the healthcare provider, wherein the pool of healthcare procedures are limited to reflect only the medical services rendered by the individual healthcare provider;

electronically selecting one or more healthcare diagnoses characteristically employed by the individual healthcare provider for inclusion in the customized form that is to be used by the healthcare provider, wherein the one or more diagnoses are reasons for performing at least one of the procedures from the pool of healthcare procedures characteristically performed by the individual healthcare provider;

generating the customized form in a generally integrated graphical display, by defining display specifications that relate to a display of the healthcare procedures characteristically performed by the individual healthcare provider and the healthcare diagnoses characteristically employed by the individual healthcare provider, wherein the display specifications are based on user preferences of the individual healthcare provider, and wherein said step for generating the customized form comprises:

using a computer processing system and interface to define a structure for the customized form, selecting a number of rows for inclusion into the customized form, wherein the rows are selectively moved up or down, obtaining aspects of the customized form from an existing customized form, determining whether to pull detail lines from the existing customized form, defining specifications relating to the pool of healthcare procedures as performed by the individual healthcare provider in the practice of the individual healthcare provider, defining specifications relating to the one or more healthcare diagnoses pertaining to the practice of the individual healthcare provider, displaying a reference to the customized form in a searchable field within a form definition window, populating one or more fields of the form definition window, displaying the form definition window with the populated fields, entering procedure and diagnosis codes curtailed to the practice of the individual healthcare provider, providing a status and an identification relating to the electronically created customized form, providing a visit form look up and description, instantaneously updating the customizable form, providing the ability to lock the customized form, and displaying a preview of the customized form; and determining a particular sequence of the pool of healthcare procedures based upon user preferences of the individual healthcare provider;

selecting at least one of (i) a diagnosis of the customized form and (ii) a procedure of the customized form, the diagnosis and the procedure being limited to reflect only those commonly rendered by the individual healthcare provider in connection with one of the healthcare procedures from the pool of healthcare procedures on a patient;

displaying billing information on a real time basis and prior to the rendering of the one of the procedures on the patient to allow the healthcare provider to advise the patient as to healthcare service to be rendered, including the most cost efficient healthcare alternative for the patient; and automatically recording an insurance code entry on an insurance invoice, the insurance code entry representing the diagnosis and the procedure selected by the specialized healthcare provider, wherein the process of selecting the diagnosis and the procedure automatically creates the insurance code entry on the insurance invoice.

2. A method as recited in claim 1, wherein the step for generating the customizable form comprises including in the customizable form at least one of:

(i) additional healthcare procedures characteristically used by another healthcare provider of the healthcare facility; and (ii) additional healthcare diagnoses characteristically employed by another healthcare provider of the healthcare facility.

3. A method as recited in claim 2, wherein the pool of healthcare procedures characteristically performed by the particular healthcare provider and the additional healthcare procedures used by another healthcare provider are limited to reflect only healthcare procedures characteristically performed by healthcare providers of the healthcare facility.

4. A method as recited in claim 2, wherein the healthcare diagnoses characteristically performed by the particular healthcare provider and the additional healthcare diagnoses employed by another healthcare provider are limited to reflect only healthcare diagnoses characteristically used by healthcare providers of the healthcare facility.

5. A method as recited in claim 1, further comprising a step for customizing the customizable form to limit the healthcare procedures of the customizable form to reflect only those healthcare procedures performed at the healthcare facility.

6. A method as recited in claim 1, wherein the step for using the customizable form includes using the customizable form to automatically create an accurate billing record statement for the patient.

7. A method as recited in claim 6, wherein the step for using the customizable form to automatically create an accurate billing record is performed in real time.

8. A method as recited in claim 7, wherein the billing record corresponds to standards established in the industry.

9. A method as recited in claim 1, wherein the step for using the customizable form comprises the steps for:
 identifying any procedures used on the patient;
 identifying any diagnoses employed to cause the procedures to be used on the patient; and
 preserving the customizable form with the identified diagnoses and procedures as part of a medical history of the patient.

10. In a system that is configured to be associated with healthcare services, a method for generating, displaying, recording and automatically billing healthcare service information, the method comprising:
 electronically selecting a pool of healthcare procedures characteristically performed by a particular healthcare provider of a healthcare facility for inclusion in a customized form for use by the healthcare provider, wherein the pool of healthcare procedures are limited to reflect only the medical services rendered by the particular healthcare provider;
 electronically selecting a healthcare diagnosis characteristically employed by the particular healthcare provider for inclusion in the customized form for use by the healthcare provider, wherein the healthcare diagnosis are limited to reflect only the medical services rendered by the particular healthcare provider, and wherein the healthcare diagnosis is a reason for performing a procedure from the pool of healthcare procedures characteristically performed by the particular healthcare provider;
 generating the customized form by defining display specifications that relate to a display of the healthcare procedures characteristically performed by the particular healthcare provider and the healthcare diagnoses characteristically employed by the particular healthcare provider, wherein the display specifications are based on user preferences of the particular healthcare provider, and wherein said step for generating the customizable form comprises:
 using a computer interface to define a new structure for the customized form, selecting a number of rows for inclusion into the customized form, wherein the rows are selectively moved up or down, obtaining aspects of the customized form from an existing customized form, determining whether to pull detail lines from the existing customized form, defining specifications relating to the pool of healthcare procedures, defining specifications relating to the healthcare diagnosis, displaying a reference to the customized form in a searchable field within a form definition window, populating one or more fields of the form definition window, displaying the form definition window with the populated fields, entering procedure and diagnosis codes, providing a status and an identification relating to the electronically created customized form, providing a visit form look up and description, instantaneously updating the customizable form, providing the ability to lock the customized form, and displaying a preview of the customized form; determining a particular sequence of the pool of healthcare procedures based upon user preferences;
 concomitantly displaying all possible healthcare procedures and healthcare diagnoses on the customized form;
 selecting at least one of (i) a diagnosis of the customized form and (ii) a procedure of the customized form, the diagnosis and the procedure being limited to reflect only those commonly rendered by the particular healthcare provider in connection with one of the healthcare procedures from the pool of healthcare procedures on a patient; and
 automatically recording an insurance code entry on an insurance invoice, the insurance code entry representing the diagnosis and the procedure selected by the specialized healthcare provider, wherein the process of selecting the diagnosis and the procedure automatically creates the insurance code entry on the insurance invoice.

11. A method as recited in claim 10, further comprising a step for rendering the customized form by (i) indicating a selection of a diagnosis of the customized form, (ii) indicating a selection of a procedure of the customized form, and (iii) indicating any cost modification for at least one of the diagnosis and the procedure indicated on the customized form different from a cost typically billed by the particular healthcare provider for the diagnosis or the procedure indicated on the customized form, and wherein the step for rendering the customized form further includes displaying billing information on a real time basis and prior to the performing of the one of the procedures on the patient to allow the healthcare provider to advise the patient as to healthcare service to be provided, including the most cost efficient healthcare alternative for the patient.

* * * * *